United States Patent
Idemaru et al.

(10) Patent No.: US 12,295,713 B2
(45) Date of Patent: May 13, 2025

(54) PERMANENT CURRENT SWITCH APPARATUS AND MAGNETIC RESONANCE IMAGING APPARATUS

(71) Applicant: CANON MEDICAL SYSTEMS CORPORATION, Otawara (JP)

(72) Inventors: Toshiki Idemaru, Ako (JP); Dai Yamashiro, Otawara (JP); Kazuto Nogami, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 162 days.

(21) Appl. No.: 18/163,326

(22) Filed: Feb. 2, 2023

(65) Prior Publication Data

US 2023/0277082 A1 Sep. 7, 2023

(30) Foreign Application Priority Data

Mar. 2, 2022 (JP) .................. 2022-031504

(51) Int. Cl.
A61B 5/055 (2006.01)
A61B 5/00 (2006.01)

(52) U.S. Cl.
CPC ............ *A61B 5/055* (2013.01); *A61B 5/0013* (2013.01)

(58) Field of Classification Search
None
See application file for complete search history.

(56) References Cited

U.S. PATENT DOCUMENTS

2006/0158795 A1* 7/2006 Tsuchiya ................ H02H 7/001
361/19

FOREIGN PATENT DOCUMENTS

| JP | 63-299214 A | 12/1988 |
| JP | 2001015821 A * | 1/2001 |
| JP | 2016119431 A * | 6/2016 |

* cited by examiner

*Primary Examiner* — Rodney E Fuller
(74) *Attorney, Agent, or Firm* — Oblon, McClelland, Maier & Neustadt, L.L.P.

(57) ABSTRACT

A permanent current switch apparatus according to an embodiment is a permanent current switch apparatus electrically connected to a superconducting coil via a superconducting wire, the permanent current switch apparatus including a plurality of parallel structures with thermal permanent current switches connected in parallel, the thermal permanent current switches being capable of switching between conducting and interrupting an electric current flowing through the superconducting wire. The parallel structures are connected in series.

8 Claims, 10 Drawing Sheets

PERMANENT CURRENT SWITCH APPARATUS AND MAGNETIC RESONANCE IMAGING APPARATUS

CROSS-REFERENCE TO RELATED APPLICATIONS

This application is based upon and claims the benefit of priority from Japanese Patent Application No. 2022-031504, filed on Mar. 2, 2022, the entire contents of which are incorporated herein by reference.

FIELD

Embodiments described herein relate generally to a permanent current switch apparatus and a magnetic resonance imaging apparatus.

BACKGROUND

Magnetic resonance imaging apparatuses have recently been provided with a superconducting magnet, which is an electromagnet using a superconductor, as a static magnetic field magnet that generates a static magnetic field in an imaging area where a subject is placed. The superconducting magnet is typically fabricated by placing a coil of a superconductor (hereinafter referred to as a "superconducting coil") in a refrigerant container filled with liquid helium serving as a refrigerant.

When cooled with the liquid helium and transitioned to a superconducting state, the superconducting coil has an electrical resistance of 0, and as a result, a large current can flow therethrough. Therefore, the superconducting magnet can generate a stronger magnetic field than an ordinary electromagnet.

DETAILED DESCRIPTION

A permanent current switch apparatus according to an embodiment is electrically connected to a superconducting coil via a superconducting wire, the permanent current switch apparatus including a plurality of parallel structures with thermal permanent current switches connected in parallel, the thermal permanent current switches being capable of switching between conducting and interrupting an electric current flowing through the superconducting wire. The parallel structures are connected in series.

Embodiments of a permanent current switch and a magnetic resonance imaging apparatus are described below in greater detail with reference to the accompanying drawings. While the embodiments below describe a case where the permanent current switch is used for a static magnetic field magnet of the magnetic resonance imaging apparatus, the embodiments are not intended to limit the present invention. In the following description, a magnetic resonance imaging apparatus is also referred to as an "MRI apparatus".

Figure 1:
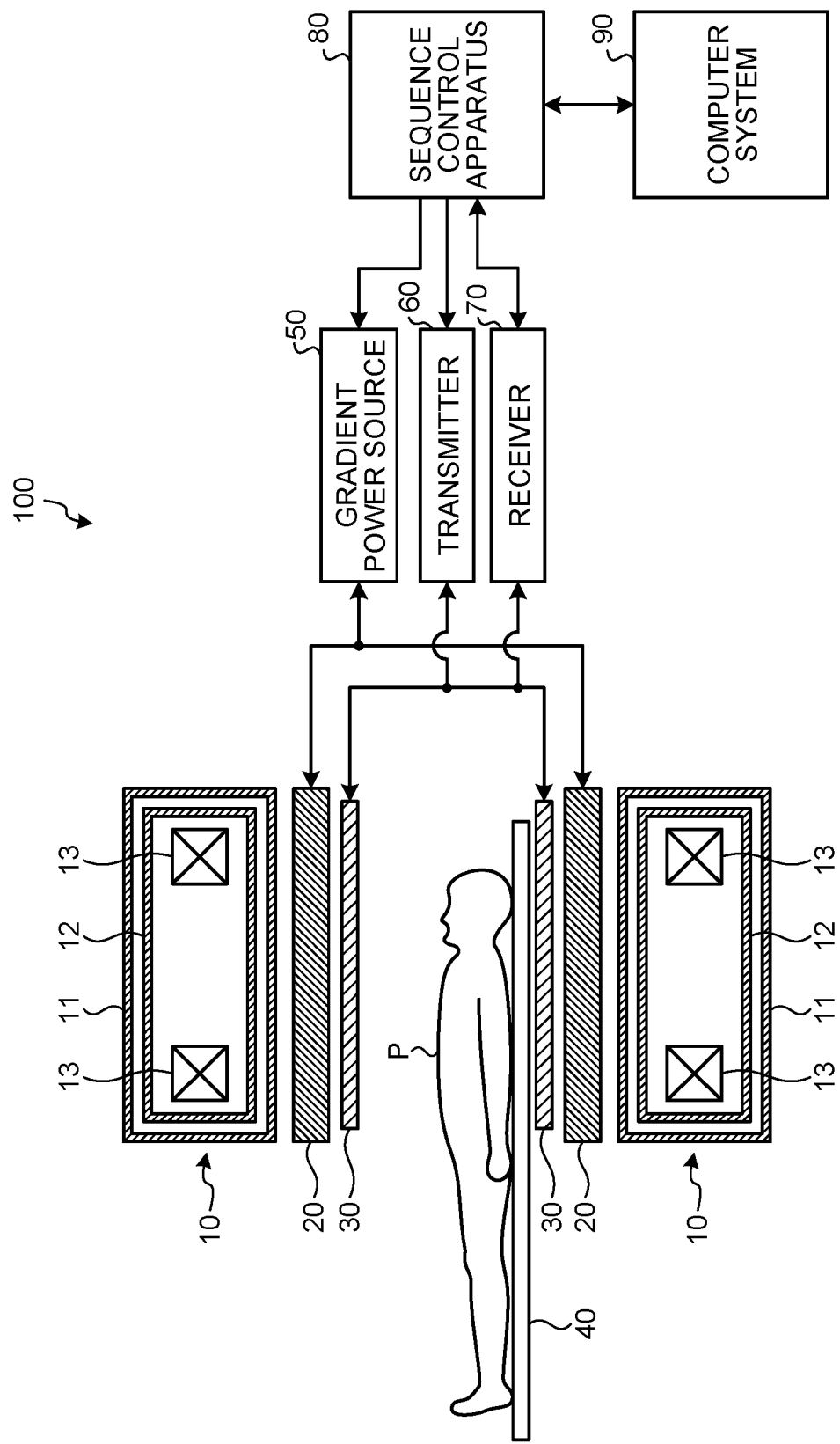
FIG. 1 is a configuration diagram of the configuration of an MRI apparatus according to an embodiment.

The configuration of an MRI apparatus 100 according to the present embodiment is described first. FIG. 1 is a configuration diagram of the configuration of the MRI apparatus 100 according to the present embodiment. As illustrated in FIG. 1, the MRI apparatus 100 includes a static magnetic field magnet 10, a gradient coil 20, an RF coil 30, a couchtop 40, a gradient power source 50, a transmitter 60, a receiver 70, a sequence control apparatus 80, and a computer system 90.

The static magnetic field magnet 10 generates a static magnetic field in an imaging area where a subject is placed. The static magnetic field magnet 10 is an example of a superconducting magnet. The static magnetic field magnet 10 includes a vacuum chamber 11, a refrigerant container 12, and a superconducting coil 13.

The vacuum chamber 11 is formed in a substantially cylindrical shape, and the inside of the cylindrical wall is maintained in a vacuum. The space formed on the inner side of the cylinder of the vacuum chamber 11 serves as the imaging area where the subject is placed. The refrigerant container 12 is formed in a substantially cylindrical shape and is housed in the vacuum chamber 11. The refrigerant container 12 contains a refrigerant, such as liquid helium, inside the wall of the cylinder. The superconducting coil 13 is disposed in the refrigerant container 12 and is immersed in the liquid helium. The superconducting coil 13 generates a static magnetic field in the imaging area on the inner side of the cylinder of the vacuum chamber 11.

The gradient coil 20 is formed in a substantially cylindrical shape and is fixed to the inner side of the static magnetic field magnet 10. The gradient coil 20 generates a gradient magnetic field in X-, Y-, and Z-axis directions set in the imaging area by an electric current supplied from the gradient power source 50.

The RF coil 30 is fixed to the inner side of the gradient coil 20 such that it faces across a subject P. The RF coil 30 irradiates the subject P with RF pulses transmitted from the transmitter 60 and receives magnetic resonance signals emitted from the subject P by excitation of hydrogen nuclei.

The couchtop 40 is horizontally movably provided on a couch, which is not illustrated, and is moved into the imaging area with the subject P placed thereon when imaging is performed. The gradient power source 50 supplies an electric current to the gradient coil 20 based on instructions from the sequence control apparatus 80.

The transmitter 60 transmits RF pulses to the RF coil 30 based on instructions from the sequence control apparatus 80. The receiver 70 detects magnetic resonance signals received by the RF coil 30 and transmits raw data obtained by digitizing the detected magnetic resonance signals to the sequence control apparatus 80.

The sequence control apparatus 80 scans the subject P by driving the gradient power source 50, the transmitter 60, and the receiver 70 under the control of the computer system 90. When receiving raw data from the receiver 70 as a result of scanning, the sequence control apparatus 80 transmits the raw data to the computer system 90.

The computer system 90 collectively controls the MRI apparatus 100. Specifically, the computer system 90 includes an input unit, a sequence controller, an image reconstructor, a storage unit, a display unit, and a main controller, for example. The input unit receives various inputs from an operator. The sequence controller causes the sequence control apparatus 80 to perform scanning based on imaging conditions input by the operator. The image reconstructor reconstructs an image based on the raw data transmitted from the sequence control apparatus 80. The storage unit stores therein the reconstructed image and other data. The display unit displays various kinds of information, such as the reconstructed image. The main controller controls operations of the functional units based on instructions from the operator.

Figure 2:
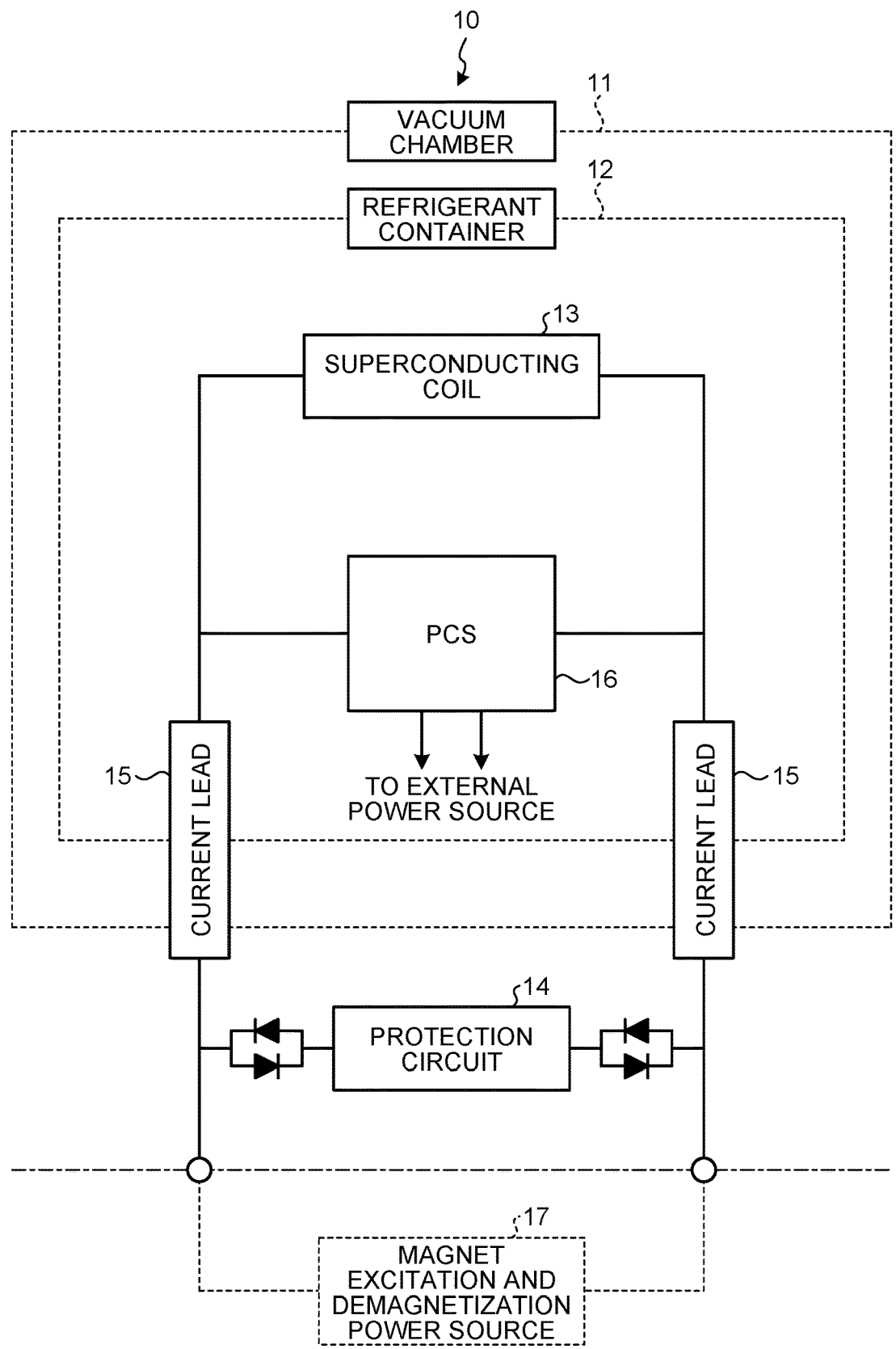
FIG. 2 is a block diagram of an example of the configuration of a static magnetic field magnet according to the embodiment.

The configuration of the static magnetic field magnet 10 is described with reference to FIG. 2. FIG. 2 is a block diagram of an example of the configuration of the static magnetic field magnet 10 according to the present embodiment. As illustrated in FIG. 2, the static magnetic field magnet 10 includes the vacuum chamber 11, the refrigerant container 12, the superconducting coil 13, a protection circuit 14, current leads 15, a PCS 16, and a magnet excitation and demagnetization power source 17.

The protection circuit 14 protects the superconducting coil 13 by consuming the electric current flowing through the superconducting coil 13 when a quench occurs in the superconducting coil 13. The protection circuit 14 is a protective resistance element or a diode bank, for example. The protection circuit 14 is disposed in a normal temperature environment outside the refrigerant container 12.

When the superconducting coil 13 is excited, in the present embodiment, the magnet excitation and demagnetization power source 17 is disconnected from the current leads 15. To demagnetize the superconducting coil 13, the magnet excitation and demagnetization power source 17 is reconnected to the current leads 15.

The current leads 15 supply an electric current from the magnet excitation and demagnetization power source 17 at room temperature (hereinafter, also referred to as normal temperature environment) to the superconducting coil 13 cooled by a refrigerant, such as liquid helium (hereinafter, also referred to as low temperature environment). The current leads 15 connect the superconducting coil 13 to the protection circuit 14. The current leads 15 are made of a high-temperature superconductor. With this structure, the current leads 15 have lower conductivity in the normal temperature state and have higher conductivity in the low temperature state.

Therefore, the current leads 15 are less likely to conduct heat during normal operation, whereby the amount of heat entering into the refrigerant container 12 from the outside can be reduced. In other words, the current leads 15 can suppress evaporation of the refrigerant caused by heat entering from the outside of the refrigerant container 12.

By contrast, when a quench occurs in the superconducting coil 13, the current leads 15 are cooled to be in a superconducting state by vaporization of the refrigerant in the refrigerant container 12. Therefore, an electric current automatically flows from the superconducting coil 13 to the protection circuit 14 via the current leads 15 when a quench occurs, whereby the protection circuit 14 can be reliably protected. In other words, the current leads 15 can serve as switches that supply an electric current from the superconducting coil 13 to the protection circuit 14 when a quench occurs.

The PCS 16 is an example of a permanent current switch apparatus. The PCS 16 according to the present embodiment is a permanent current switch apparatus including a superconducting wire 163 including switch parts 161, which will be described later, and thermal permanent current switches 160 (refer to FIG. 3). The switch part 161 is a part of the superconducting wire 163 serving as a switch that switches the superconducting wire 163 between a superconducting state and a normal conducting state by heat emitted by a heater. The PCS 16 is turned on when the switch part 161 is in the superconducting state and is turned off when the switch part 161 is in the normal conducting state. The PCS 16 is connected in parallel to the superconducting coil 13.

When the PCS 16 is turned on, the superconducting coil 13 and the PCS 16 form a closed loop if the magnet excitation and demagnetization power source 17 is disconnected, for example. When the PCS 16 is turned off, the magnet excitation and demagnetization power source 17 can supply an electric current to the superconducting coil 13, for example.

When the PCS 16 is turned on, in the present embodiment, the state of the magnet excitation and demagnetization power source 17 transitions to a disconnected state. The state of the magnet excitation and demagnetization power source 17, however, is not limited thereto. The magnet excitation and demagnetization power source 17 may have an output of close to 0, for example. In other words, the magnet excitation and demagnetization power source 17 simply needs to be in such a state that the superconducting coil 13 and the PCS 16 can form a closed loop.

The PCS 16 also includes heaters 162 (refer to FIG. 3), which will be described later. The heater 162 is connected to an external power source outside the static magnetic field magnet 10. To excite and demagnetize the superconducting coil 13, the heater 162 controls turning on/off the PCS 16 by raising and lowering the temperature of the switch part 161. The configuration of the PCS 16 will be described later.

The magnet excitation and demagnetization power source 17 is a power source used to excite or demagnetize the superconducting coil 13. The magnet excitation and demagnetization power source 17 is disposed in a normal temperature environment outside the refrigerant container 12. When the superconducting coil 13 is excited or demagnetized, the magnet excitation and demagnetization power source 17 is connected to the superconducting coil 13 via the current leads 15.

When the superconducting coil 13 is excited or demagnetized, the refrigerant in the refrigerant container 12 evaporates because the heaters 162 emit heat to control the PCS 16. The number of switch parts 161 of the PCS 16 is determined by considering the amount of evaporation of the refrigerant because refrigerants are typically expensive.

At this time, the evaporated refrigerant cools the current leads 15 and brings them into a superconducting state.

Therefore, when the superconducting coil 13 is excited or demagnetized, the magnet excitation and demagnetization power source 17 can stably supply an electric current to the superconducting coil 13 via the current leads 15.

The configuration of the PCS 16 is specifically described with reference to FIGS. 3 to 10. The configuration of a PCS 216 different from the PCS 16 according to the present embodiment is described first with reference to FIG. 7 by way of comparison with the configuration of the PCS 16 illustrated in FIG. 3. FIG. 7 is a schematic of the configuration of the PCS 216 different from the PCS 16 according to the present embodiment.

As illustrated in FIG. 7, the PCS 216 includes thermal permanent current switches PC1 to PC8, a superconducting wire SU, and a heater connecting wire HL, for example. In the following description, the thermal permanent current switches PC1 to PC8 may be referred to simply as thermal permanent current switches PC when they are not particularly distinguished.

The thermal permanent current switch PC1 includes a switch part SW1 and a heater HT1. In the following description, the switch parts SW1 to SW8 may be referred to simply as switch parts SW when they are not particularly distinguished. The heaters HT1 to HT8 may be referred to simply as heaters HT when they are not particularly distinguished. The switch part SW is a part serving as a switch that switches the switch part SW between the superconducting state and the normal conducting state by heat emitted by the heater HT.

The thermal permanent current switch PC switches between conducting and interrupting an electric current flowing through the switch part SW. The thermal permanent current switches PC1 to PC4 are connected in series to constitute a switch series structure IL1. Similarly, the thermal permanent current switches PC5 to PC8 constitute a switch series structure IL2. The switch series structure IL1 and the switch series structure IL2 are connected in parallel by the superconducting wire SU.

The heater HT heats the switch part SW. The thermal permanent current switch PC switches the switch part SW between the superconducting state and the normal conducting state by adjusting the heating of the heater HT and raising and lowering the temperature of the switch part SW. The heater HT is connected in series to an external power source PW by the heater connecting wire HL.

The following describes the state of the electric current in a case where a quench occurs in the thermal permanent current switch PC when the PCS 216 is in the superconducting state. First, a case where no quench occurs in any of the thermal permanent current switches PC1 to PC8 is described.

In this case, when the electric current flowing through the PCS 216 is Isc, the electric current Isc is divided between the switch series structure IL1 and the switch series structure IL2 connected in parallel as illustrated in FIG. 7. Therefore, the electric current flowing through the switch series structure IL1 is approximately Isc/2, and the electric current flowing through the switch series structure IL2 is approximately Isc/2. Next, a case where a quench occurs in any one of the thermal permanent current switches PC1 to PC8 is described.

Figure 4:
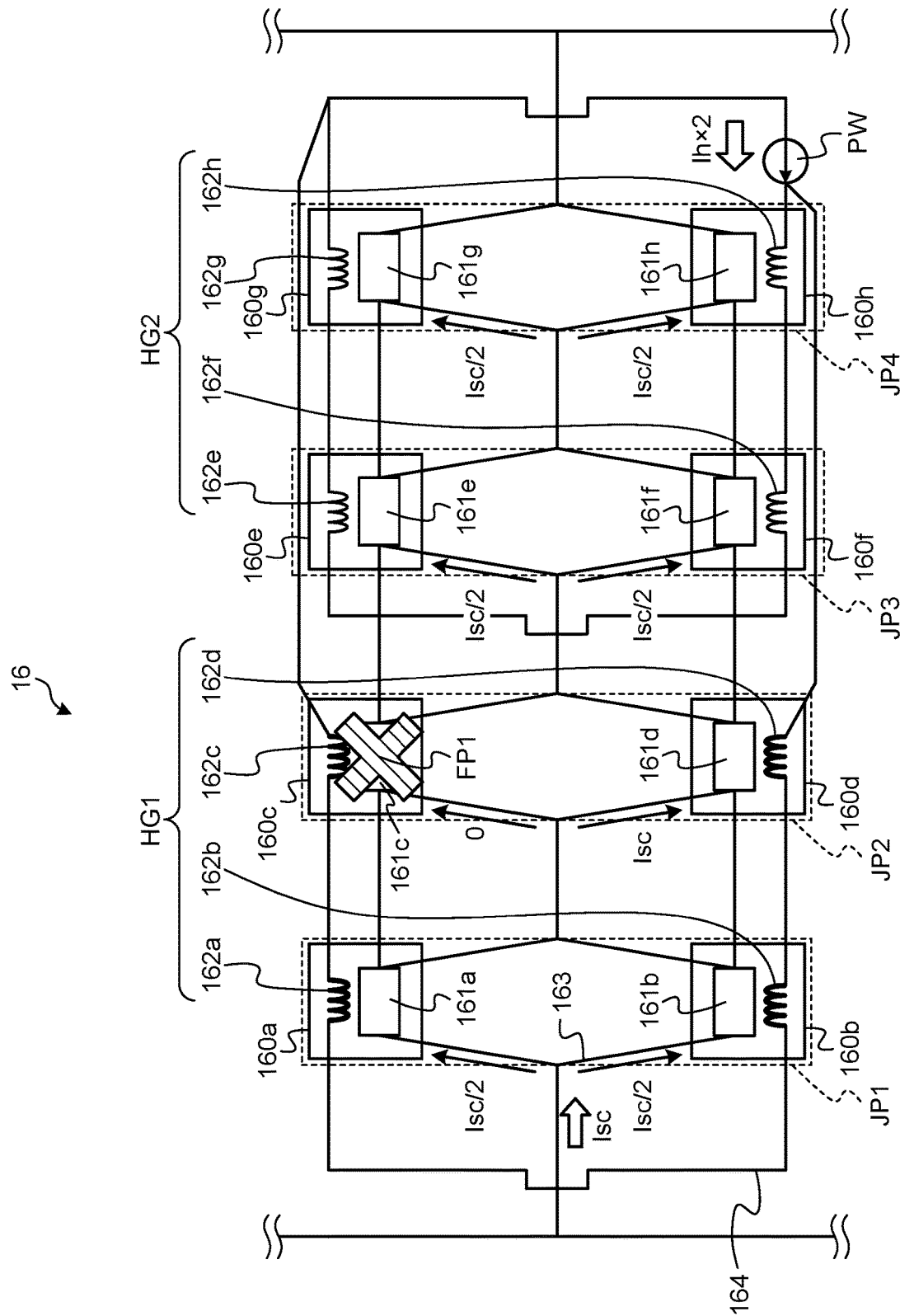
FIG. 4 is a schematic of an example of a current change when a quench occurs in one of thermal permanent current switches included in the PCS according to the embodiment.
Figure 8:
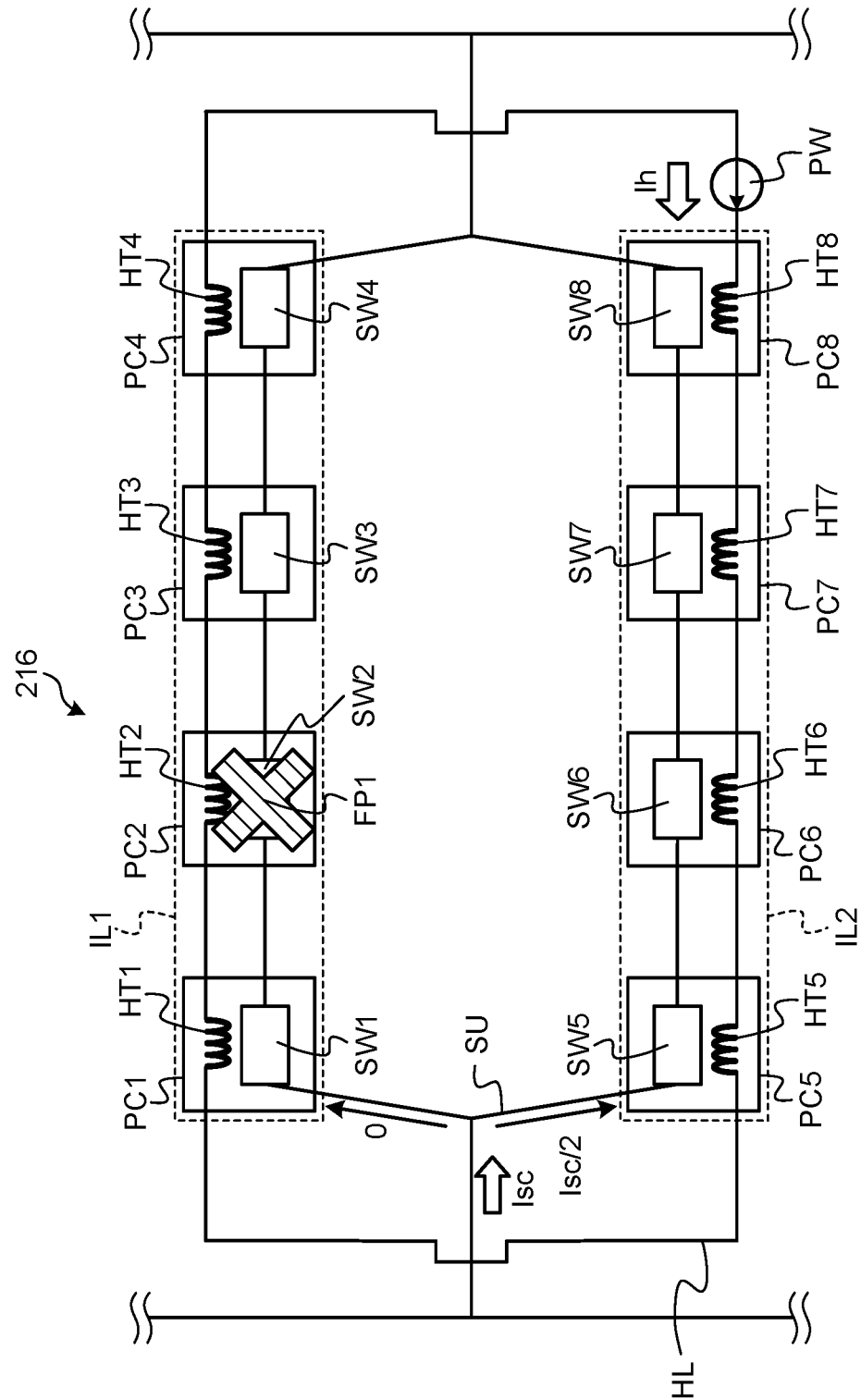
FIG. 8 is a schematic of a current change when a quench occurs in one of the thermal permanent current switches included in the PCS different from the PCS according to the embodiment.

FIG. 8 illustrates the configuration of the PCS 216 different from the PCS 16 according to the present embodiment by way of comparison with the configuration of the PCS 16 illustrated in FIG. 4. FIG. 8 is a schematic of the state of the electric current when a quench occurs in one of the thermal permanent current switches PC included in the PCS 216 different from the PCS 16 according to the embodiment. FIG. 8 illustrates a case where a quench occurs in the thermal permanent current switch PC2 constituting the switch series structure IL1 due to failure FP1. In this case, the thermal permanent current switch PC2 serves as a resistance R When the thermal permanent current switch PC2 serves as the resistance R, all the electric current flowing through the PCS 216 is commutated to the switch series structure IL2 composed of the thermal permanent current switches PC5 to PC8 where no quench occurs as illustrated in FIG. 8. Therefore, the electric current flowing through the switch series structure IL1 is 0, and the electric current flowing through the switch series structure IL2 is Isc/2.

As a result, the PCS 216 can maintain the superconducting state of one of the paths, thereby maintaining the operation of the static magnetic field magnet 10 in a permanent current mode. In other words, the PCS 216 in this case is redundant because it can maintain the operation of the static magnetic field magnet 10 in the permanent current mode if a quench occurs in any one of the thermal permanent current switches PC1 to PC8.

Next, a case where a quench occurs in each of the switch series structure IL1 and the switch series structure IL2 is described.

Figure 5:
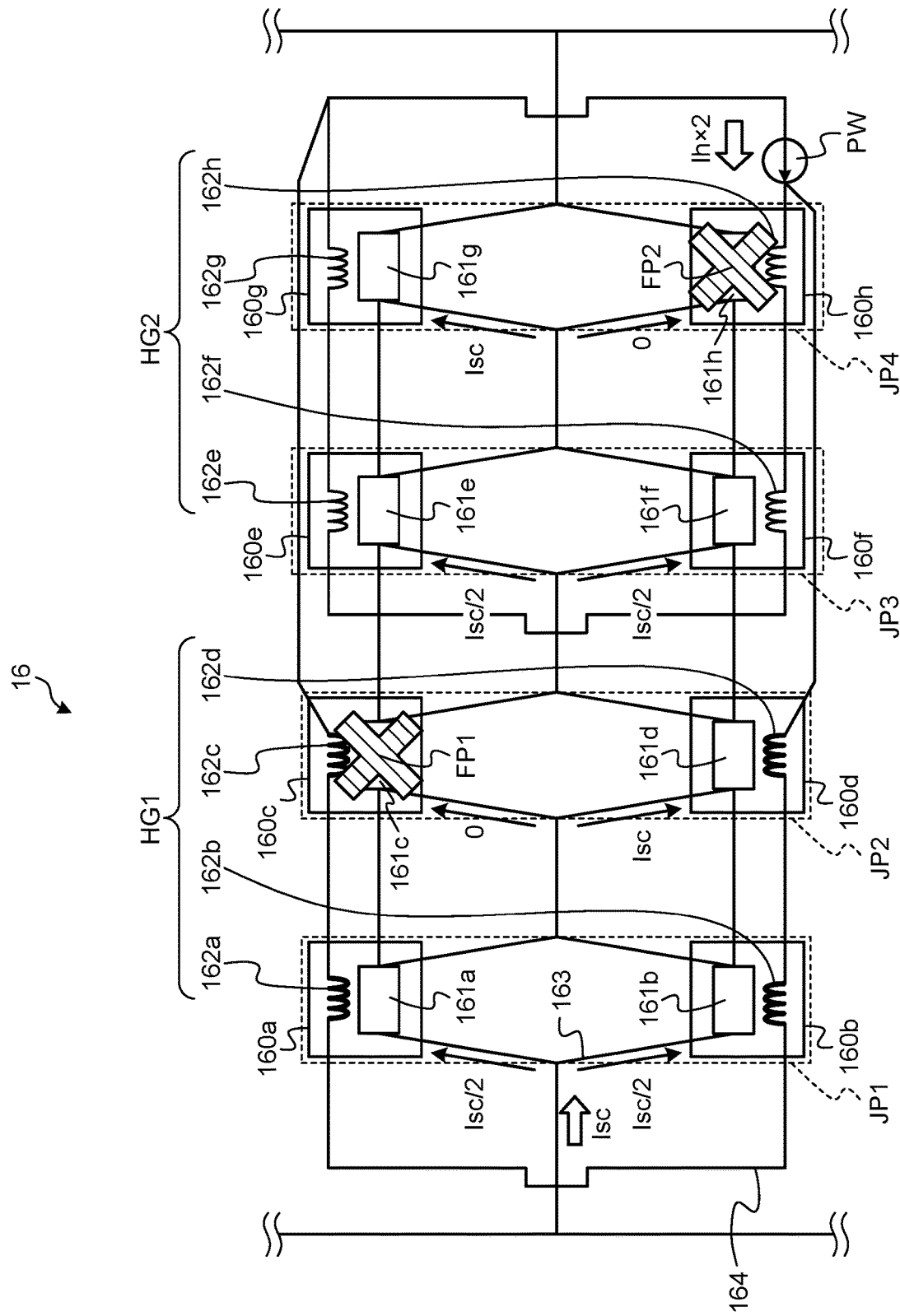
FIG. 5 is a schematic of an example of a current change when quenches occur in two of the thermal permanent current switches included in the PCS according to the embodiment.
Figure 9:
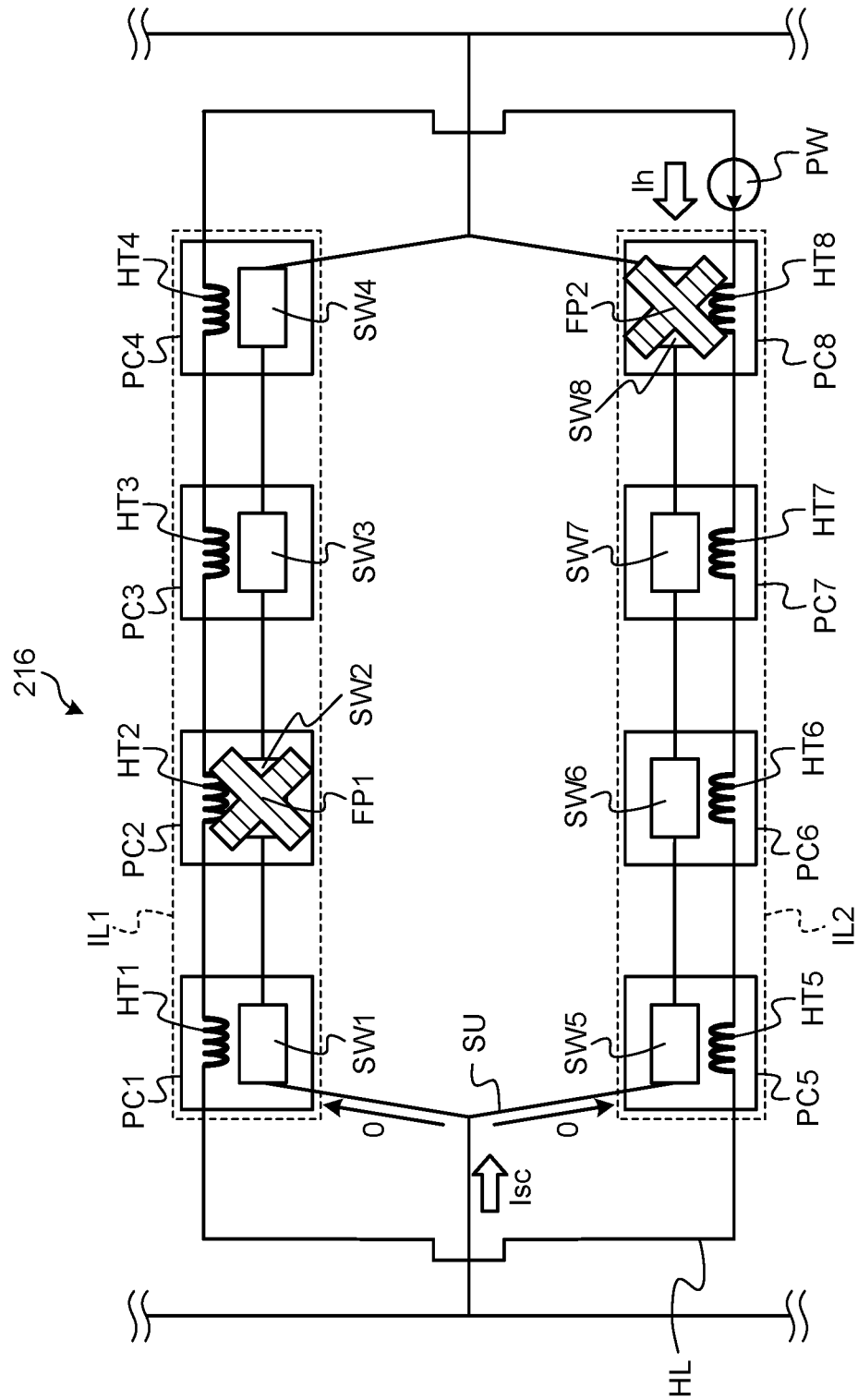
FIG. 9 is a schematic of a current change when quenches occur in two of the thermal permanent current switches included in the PCS different from the PCS according to the embodiment.

FIG. 9 illustrates the configuration of the PCS 216 different from the PCS 16 according to the present embodiment by way of comparison with the configuration of the PCS 16 illustrated in FIG. 5. FIG. 9 is a schematic of the state of the electric current when a quench occurs in each of the switch series structure IL1 and the switch series structure IL2 included in the PCS 216 different from the PCS 16 according to the embodiment. FIG. 9 illustrates a state where a quench occurs in the thermal permanent current switch PC2 constituting the switch series structure IL1 due to failure FP1, and a quench occurs in the thermal permanent current switch PC8 constituting the switch series structure IL2 due to failure FP2.

In this case, the thermal permanent current switch PC2 and the thermal permanent current switch PC8 serve as resistances R. When the thermal permanent current switch PC2 and the thermal permanent current switch PC8 serve as the resistances R, the redundancy of the PCS 216 is lost, and the electric current Isc flowing through the PCS 216 is attenuated and decreases to 0 as illustrated in FIG. 9.

In other words, if a quench occurs in the thermal permanent current switch PC of one of the switch series structures IL1 and IL2 while a quench is occurring in the thermal permanent current switch PC of the other, the static magnetic field magnet 10 fails to maintain the operation in the permanent current mode.

In addition, the configuration of the PCS 216 different from the PCS 16 has the problem of failing to excite or demagnetize the superconducting coil 13 if the heater connecting wire HL is not conductive due to disconnection or other causes. The following describes the effects caused when disconnection occurs in the heater connecting wire HL included in the PCS 216 different from the PCS 16.

Figure 6:
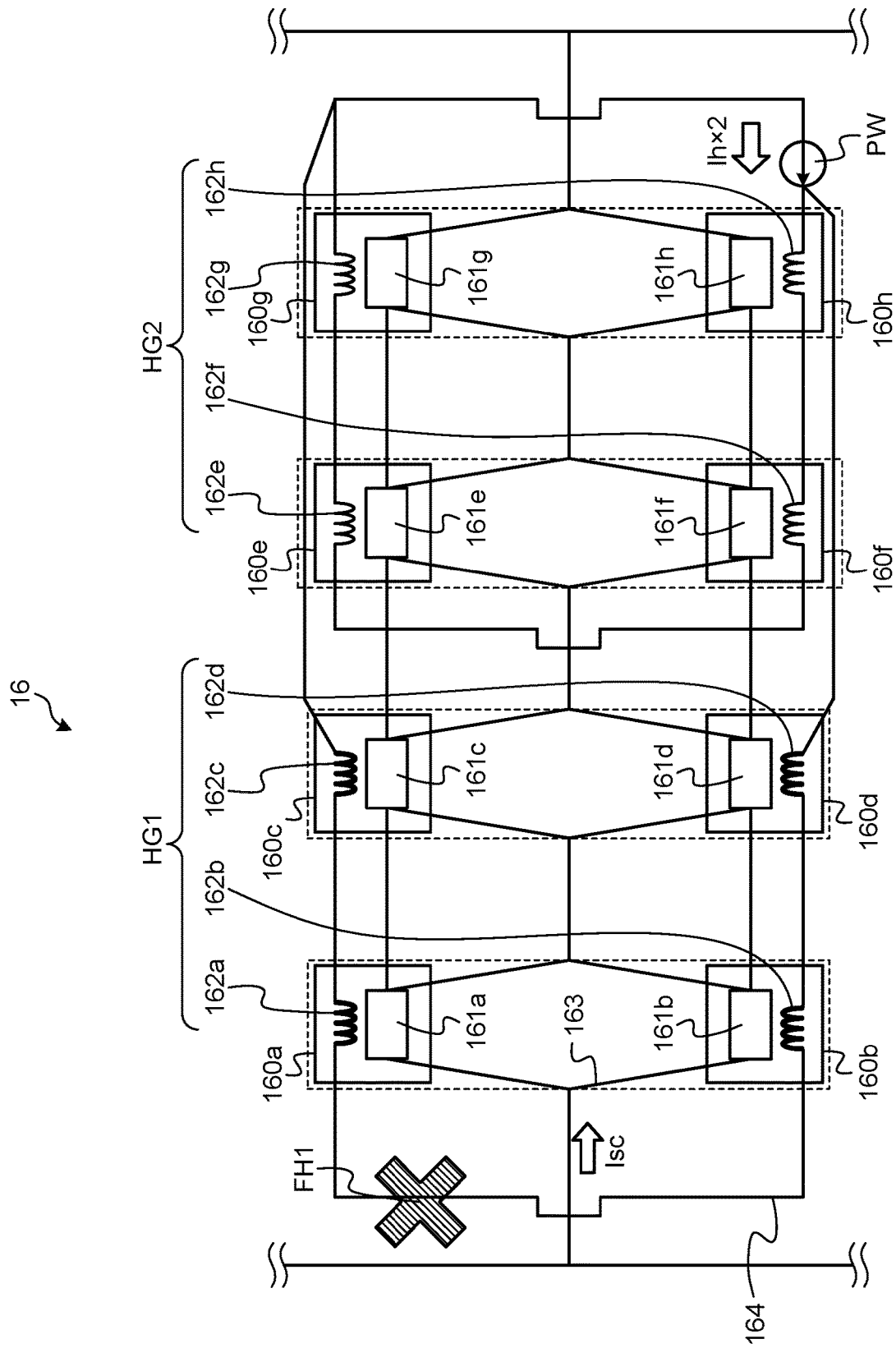
FIG. 6 is a schematic of an example of a case where disconnection occurs in a heater connecting wire included in the PCS according to the embodiment.
Figure 7:
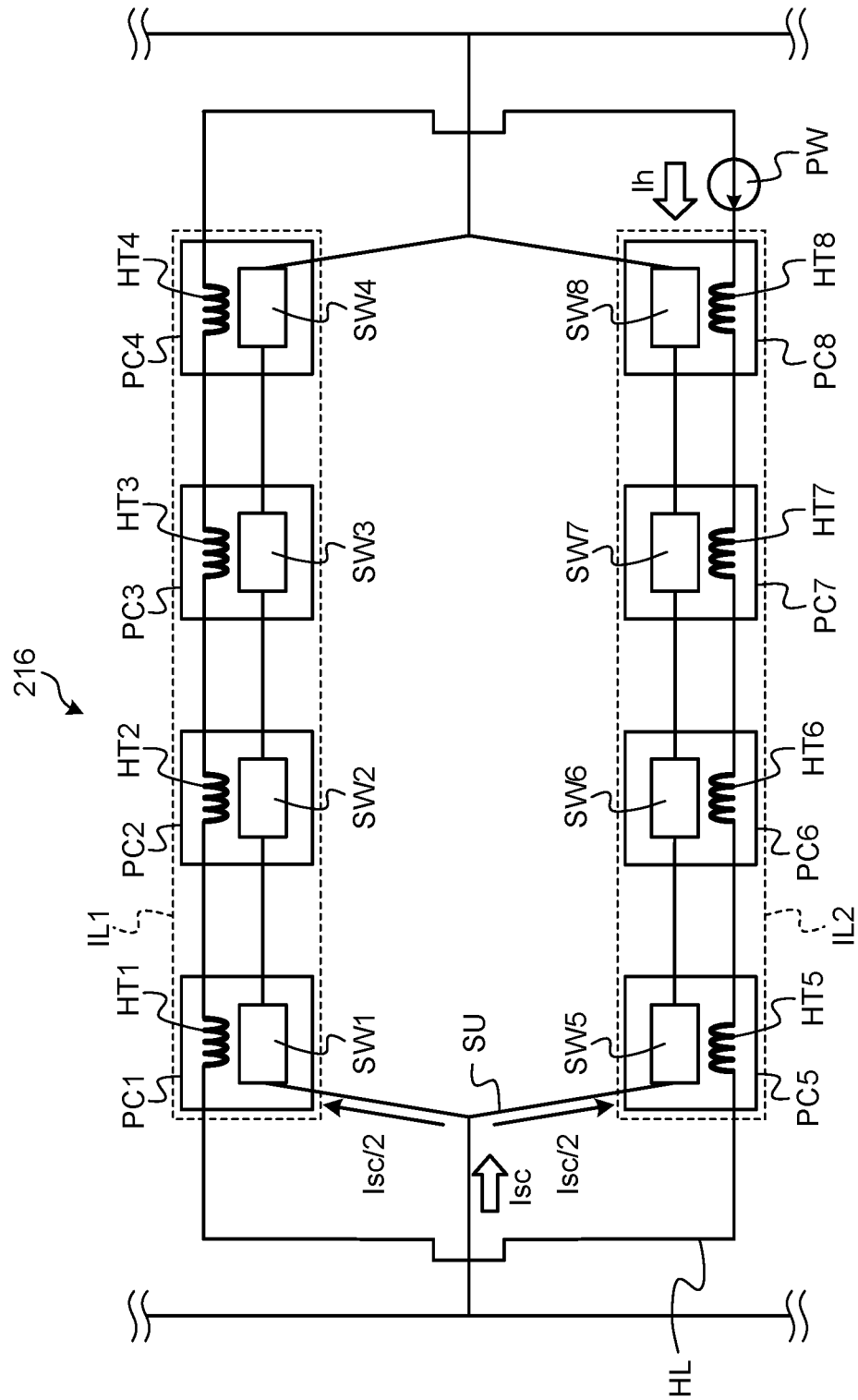
FIG. 7 is a schematic of the configuration of a PCS different from the PCS according to the embodiment.
Figure 10:
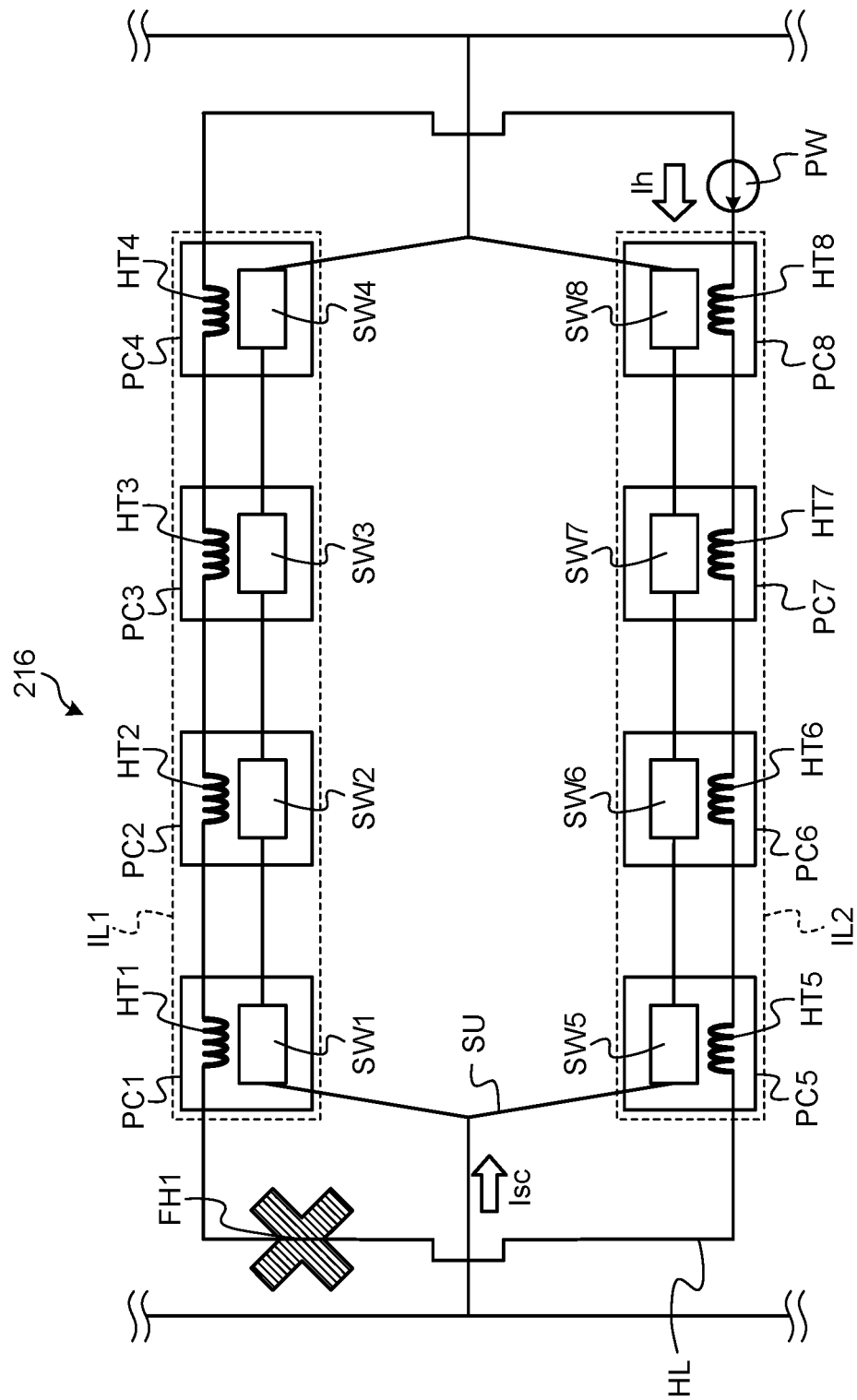
FIG. 10 is a schematic of a case where disconnection occurs in the heater connecting wire included in the PCS different from the PCS according to the embodiment.

FIG. 10 illustrates the configuration of the PCS 216 different from the PCS 16 according to the present embodiment by way of comparison with the configuration of the PCS 16 illustrated in FIG. 6. FIG. 10 is a schematic of a state where disconnection occurs in the heater connecting wire HL included in the PCS 216 different from the PCS 16 according to the embodiment. FIG. 10 illustrates a case where disconnection occurs at part of the heater connecting wire HL due to failure FH1.

If disconnection occurs in part of the heater connecting wire HL, a heater current Ih fails to be applied to the heaters HT1 to HT8 because the heaters HT1 to HT8 are connected in series to the external power source PW. As described above, the PCS 216 switches the switch parts SW between the superconducting state and the normal conducting state by adjusting the heating of the heaters HT1 to HT8 and raising and lowering the temperature of the superconducting wire SU.

In other words, if disconnection occurs in part of the heater connecting wire HL, the PCS 216 fails to adjust the heating of the heater HT1 and raise and lower the temperature of the superconducting wire SU. As a result, the static magnetic field magnet 10 fails to excite or demagnetize the superconducting coil 13.

To address this, the PCS 16 according to the present embodiment has a configuration to solve the problem of the PCS 216 different from the PCS 16 described above. Specifically, in the PCS 16 according to the present embodiment, a plurality of switch parallel structures each composed of a plurality of thermal permanent current switches connected in parallel are connected in series. The switch parallel structure is an example of a parallel structure. The following describes the configuration of the PCS 16 according to the present embodiment with reference to FIG. 3.

Figure 3:
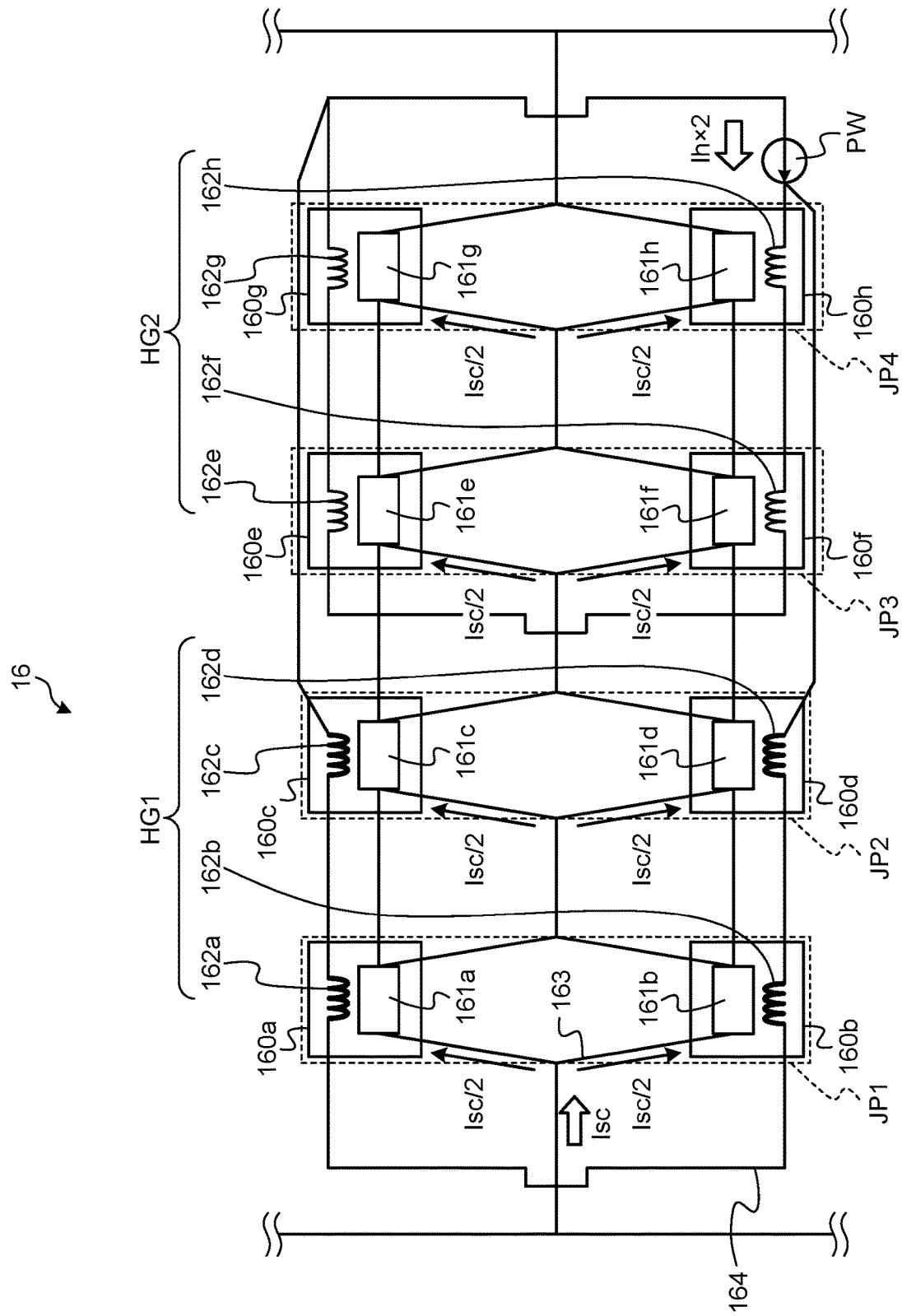
FIG. 3 is a schematic of an example of the configuration of a PCS according to the embodiment.

FIG. 3 is a schematic of an example of the configuration of the PCS 16 according to the embodiment. As illustrated in FIG. 3, the PCS 16 includes thermal permanent current switches 160*a* to 160*h*, a superconducting wire 163, and a heater connecting wire 164. In the following description, the thermal permanent current switches 160*a* to 160*h* may be referred to simply as thermal permanent current switches 160 when they are not particularly distinguished.

Similarly to the PCS 216 different from the PCS 16, the thermal permanent current switch 160 switches between conducting and interrupting an electric current flowing through the superconducting wire 163. The thermal permanent current switches 160*a* and 160*b* are connected in parallel by the superconducting wire 163 to constitute a switch parallel structure JP1.

Similarly, the thermal permanent current switches 160*c* and 160*d* constitute a switch parallel structure JP2, the thermal permanent current switches 160*e* and 160*f* constitute a switch parallel structure JP3, and the thermal permanent current switches 160*g* and 160*h* constitute a switch parallel structure JP4. The switch parallel structures JP1, JP2, JP3, and JP4 are connected in series by the superconducting wire 163.

While the superconducting wire 163 according to the present embodiment is made of Cu/NbTi, the material of the superconducting wire 163 is not limited thereto. The superconducting wire 163 may be made of CuNi/NbTi, for example.

The thermal permanent current switch 160*a* includes a switch part 161*a* and a heater 162*a*. In the following description, the switch parts 161*a* to 161*h* may be referred to simply as switch parts 161 when they are not particularly distinguished. The heaters 162*a* to 162*h* may be referred to simply as heaters 162 when they are not particularly distinguished.

Similarly to the switch part SW of the PCS 216 different from the PCS 16, the switch part 161 is a part serving as a switch that switches the switch part 161 between the superconducting state and the normal conducting state by heat emitted by the heater 162.

In the present embodiment, while the switch part 161 is fabricated by removing Cu from Cu/NbTi constituting the superconducting wire 163, the configuration of the switch part 161*a* is not limited thereto. The switch part 161*a* may be made of CuNi/NbTi, for example. Similarly to the heater HT of the PCS 216 different from the PCS 16, the heater 162 heats the superconducting wire 163.

The heaters 162 are divided into a plurality of groups and are connected in parallel to the external power source PW. The heaters 162 are connected such that the electric current flowing through the heaters 162 is equal. In the PCS 16, for example, the electric current flowing through the heaters 162 is made equal by making the number of heaters 162 connected in parallel to the external power source PW by the heater connecting wire 164 equal.

With this configuration, the heaters can heat the superconducting wire 163 at the corresponding positions without generating any temperature difference. Therefore, the switch parts 161 can switch the switch parts 161 at the corresponding positions between the superconducting state and the normal conducting state at substantially the same timing.

In the present embodiment, the heaters 162*a*, 162*b*, 162*c*, and 162*d* constitute a heater group HG1. The heaters 162*e*, 162*f*, 162*g*, and 162*h* constitute a heater group HG2. The heater group HG1 and the heater group HG2 are connected in parallel to the external power source PW by the heater connecting wire 164 independent of the superconducting wire 163.

The parallel connection configuration of the heaters 162 is not limited to the configuration described above. For example, the number of heaters 162 of the heater group HG1 may be two, and the number of heaters 162 of the heater group HG2 may be six in the example described above. The number of heater groups is not limited to two. The number of heater groups may be three or more, for example.

The following describes the state of the electric current when a quench occurs in the thermal permanent current switch 160 when the PCS 16 having the configuration described above is in the superconducting state. First, a case where no quench occurs in any of the thermal permanent current switches 160*a* to 160*h* is described.

In this case, when the electric current flowing through the PCS 16 is Isc, the electric current Isc is divided between the thermal permanent current switches 160 connected in parallel as illustrated in FIG. 3. Therefore, the electric current flowing through the thermal permanent current switch 160*a* of the switch parallel structure JP1 is approximately Isc/2, and the electric current flowing through the thermal permanent current switch 160*b* is approximately Isc/2.

Similarly, the electric current flowing through the thermal permanent current switch 160*c* of the switch parallel structure JP2 is approximately Isc/2, and the electric current flowing through the thermal permanent current switch 160*d* is approximately Isc/2. Similarly, the electric current flowing through the thermal permanent current switch 160*e* of the switch parallel structure JP3 is approximately Isc/2, and the electric current flowing through the thermal permanent current switch 160*f* is approximately Isc/2. Similarly, the electric current flowing through the thermal permanent current switch 160*g* of the switch parallel structure JP4 is approximately Isc/2, and the electric current flowing through the thermal permanent current switch 160*h* is approximately Isc/2.

Next, a case where a quench occurs in any one of the thermal permanent current switches 160 is described with reference to FIG. 4.

FIG. 4 is a schematic of an example of a current state when a quench occurs in one of the thermal permanent current switches 160 included in the PCS 16 according to the embodiment. FIG. 4 illustrates a case where a quench occurs in the thermal permanent current switch 160c constituting the switch parallel structure JP2 due to failure FP1. In this case, the thermal permanent current switch 160c serves as a resistance R.

When the thermal permanent current switch 160c serves as the resistance R, all the electric current flowing through the switch parallel structure JP2 is commutated to the thermal permanent current switch 160d where no quench occurs as illustrated in FIG. 4. Therefore, the electric current flowing through the thermal permanent current switch 160c is 0, and the electric current flowing through the thermal permanent current switch 160d is Isc. The electric current flowed through the thermal permanent current switch 160d is transmitted to the switch parallel structure JP3 in the subsequent stage.

As a result, the PCS 16 can maintain the superconducting state of the superconducting wire 163, thereby maintaining the operation of the static magnetic field magnet 10 in the permanent current mode. In other words, the PCS 16 is redundant because it can maintain the operation of the static magnetic field magnet 10 in the permanent current mode if a quench occurs in any one of the thermal permanent current switches 160a to 160h.

Next, a case where quenches occur in any two of the thermal permanent current switches 160 is described with reference to FIG. 5.

FIG. 5 is a schematic of an example of a current state when quenches occur in two of the thermal permanent current switches included in the PCS 16 according to the embodiment. FIG. 5 illustrates a state where a quench occurs in the thermal permanent current switch 160h constituting the switch parallel structure JP4 due to failure FP2 while a quench is occurring in the thermal permanent current switch 160c constituting the switch parallel structure JP2 due to failure FP1. In this case, the thermal permanent current switch 160h serves as a resistance R When the thermal permanent current switch 160h serves as the resistance R, all the electric current flowing through the switch parallel structure JP3 is commutated to the thermal permanent current switch 160g where no quench occurs as illustrated in FIG. 5. Therefore, the electric current flowing through the thermal permanent current switch 160g is Isc, and the electric current flowing through the thermal permanent current switch 160h is 0.

As a result, the PCS 16 effectively functions and maintains the superconducting state of the superconducting wire 163, whereby the operation of the static magnetic field magnet 10 in the permanent current mode can be maintained. In other words, the PCS 16 is redundant because it can maintain the operation of the static magnetic field magnet 10 in the permanent current mode if quenches occur in two of the thermal permanent current switches 160c and 160h.

If a quench occurs in the thermal permanent current switch 160d while a quench is occurring in the thermal permanent current switch 160c constituting the switch parallel structure JP2, the thermal permanent current switch 160d serves as a resistance R, which is not illustrated. When the thermal permanent current switch 160c and the thermal permanent current switch 160d serve as the resistances R, the redundancy of the PCS 16 is lost, and the electric current Isc is attenuated by the resistances R and decreases to 0.

Therefore, the PCS 16 according to the present embodiment can maintain the operation of the static magnetic field magnet 10 in the permanent current mode if quenches occur in any two of the thermal permanent current switches 160 as long as the quenches do not occur in either of the thermal permanent current switches 160 constituting the same switch parallel structure JP.

The following describes the difference in unreliability between the PCS 16 according to the present embodiment and the PCS 216 different from the PCS 16 using the PCS 16 according to the present embodiment described with reference to FIGS. 3 to 6 and the PCS 216 different from the PCS 16 described with reference to FIGS. 7 to 10 as examples. In the present embodiment, the unreliability indicates the degree to which the permanent current mode fails to be maintained by quenches in two thermal permanent current switches in any desired period of time (e.g., ten years).

When the failure probability per thermal permanent current switch PC or 160 in two-parallel connection is F2, and the failure probability per thermal permanent current switch PC or 160 in one-parallel connection is F1, for example, unreliability F of the PCS 216 is expressed by $F=8C1 \times F2 \times 4C1 \times F1$. By contrast, the unreliability F of the PCS 16 is expressed by $F=8C1 \times F2 \times F1$. Thus, the unreliability of the PCS 16 is one fourth of that of the PCS 216.

In other words, the PCS 16 according to the present embodiment has higher reliability than the PCS 216 different from the PCS 16.

The following describes the effects caused when disconnection occurs in the heater connecting wire 164 included in the PCS 16 according to the present embodiment with reference to FIG. 6. FIG. 6 is a schematic of an example of a case where disconnection occurs in the heater connecting wire 164 included in the PCS 16 according to the embodiment.

FIG. 6 illustrates a case where disconnection occurs in part of the heater connecting wire 164 due to failure FH1. If disconnection occurs at the position of the failure FH1, the external power source PW fails to apply the heater current Ih to the heaters 162 constituting the heater group HG1.

If disconnection occurs at the position of the failure FH1, however, the external power source PW can apply the heater current Ih to the heater group HG2 because the heater group HG1 and the heater group HG2 in the PCS 16 are connected in parallel to the external power source PW. In other words, the static magnetic field magnet 10 according to the present embodiment can excite and demagnetize the superconducting coil 13 if disconnection occurs at one position of the heater connecting wire 164.

As described above, the MRI apparatus 100 according to the present embodiment includes the static magnetic field magnet 10 having the superconducting coil 13 and the PCS 16. The PCS 16 is connected in parallel to the superconducting coil 13 and includes the superconducting wire 163. The PCS 16 includes the switch parallel structure JP in which a plurality of thermal permanent current switches 160 that interrupt an electric current flowing through the superconducting wire 163 are connected in parallel. A plurality of switch parallel structures JP are connected in series.

With this configuration, if a quench occurs in one of the thermal permanent current switches 160 constituting the switch parallel structure JP, the electric current can flow through another thermal permanent current switch 160 constituting the switch parallel structure JP. Therefore, the PCS 16 can maintain the superconducting state of the superconducting coil 13. In other words, the PCS 16 according to the present embodiment is redundant and can improve the reliability of the static magnetic field magnet 10 compared with the case where the thermal permanent current switches 160 are connected in series to the superconducting coil 13.

In the PCS 16 according to the present embodiment, a plurality of switch parallel structures JP are connected in series. With this configuration, if one thermal permanent current switch 160 is quenched while another thermal permanent current switch is being quenched, the PCS 16 can maintain the superconducting state of the superconducting coil unless all the thermal permanent current switches 160 constituting the same switch parallel structure JP are quenched. Therefore, the PCS 16 according to the present embodiment can increase the possibility of maintaining the superconducting state of the superconducting coil 13 if two or more thermal permanent current switches 160 are quenched. In other words, the PCS 16 according to the present embodiment can further improve the reliability of the static magnetic field magnet 10.

The PCS 16 according to the present embodiment includes a plurality of the heaters 162 and the heater connecting wire 164. The heaters 162 raise or lower the temperature of the respective switch parts 161. The heater connecting wire 164 connects the heaters 162 in parallel to the external power source PW that supplies electric power to the heaters 162.

With this configuration, the thermal permanent current switch 160 can switch the switch part 161 between the superconducting state and the normal conducting state by adjusting the heating of the heater 162 and raising and lowering the temperature of the switch part 161. Therefore, the static magnetic field magnet 10 according to the present embodiment can excite and demagnetize the superconducting coil 13 by the thermal permanent current switches 160.

In the PCS 16 according to the present embodiment, the external power source PW and the heaters 162 are connected in parallel. With this configuration, if disconnection occurs at one position of the heater connecting wire 164, the PCS 16 can apply an electric current to the heaters 162 on the side where no disconnection occurs. In other words, the static magnetic field magnet 10 according to the present embodiment can excite and demagnetize the superconducting coil 13 if disconnection occurs at one position of the heater connecting wire 164.

In the PCS 16 according to the present embodiment, the heaters 162 are connected in parallel by the heater connecting wire 164 such that the electric current flowing through the heaters 162 is equal. With this configuration, the heaters can heat the superconducting wire 163 at the corresponding positions without generating any temperature difference. Therefore, the switch parts 161 can switch the switch parts 161 at the corresponding positions between the superconducting state and the normal conducting state at substantially the same timing.

In the PCS 16 according to the present embodiment, the number of heaters 162 connected in parallel by the heater connecting wire 164 is equal. This configuration can facilitate making the electric current flowing through the heaters 162 equal.

The embodiment described above can be appropriately modified by changing some of the components or functions of each apparatus. The following describes some modifications according to the embodiment described above as other embodiments. In the following description, the points different from the embodiment described above are mainly explained, and detailed explanation of the points common to the already explained contents is omitted. The modifications to be described below may be implemented individually or in combination as appropriate.

First Modification

In the embodiment above, the PCS 16 in which four switch parallel structures JP each composed of two thermal permanent current switches 160 are connected in series has been described. The configuration of the PCS 16, however, is not limited thereto. In the PCS 16, for example, three switch parallel structures JP each composed of three thermal permanent current switches 160 may be connected in series.

The PCS 16 can maintain the superconducting state of the superconducting coil 13 unless all of the thermal permanent current switches 160 constituting the same switch parallel structure JP are quenched. Therefore, by increasing the number of thermal permanent current switches 160 constituting the switch parallel structure JP, the PCS 16 can increase the possibility that the superconducting state of the superconducting coil 13 can be maintained even if quenches occur in a plurality of thermal permanent current switches 160.

In other words, the PCS 16 according to the present modification can further improve the reliability of the static magnetic field magnet 10.

Second Modification

In the embodiment above, the PCS 16 in which two heater groups HG each composed of four heaters 162 are connected in parallel has been described. The parallel connection configuration of the heaters 162 of the PCS 16, however, is not limited thereto. In the PCS 16, for example, four heater groups HG each composed of two heaters 162 may be connected in parallel.

In the PCS 16, the heaters 162 are connected in parallel. With this configuration, if disconnection occurs in the heater connecting wire 164, but there is a heater group HG where no disconnection occurs, the PCS 16 can apply the electric current to the heaters 162 constituting the heater group HG. Therefore, by increasing the number of groups of the heaters 162 connected in parallel, the PCS 16 can increase the possibility that the superconducting coil 13 can be excited and demagnetized if disconnection occurs in the heater connecting wire 164.

In other words, the PCS 16 according to the present modification can increase the possibility that the superconducting coil 13 can be excited and demagnetized if disconnection occurs in the heater connecting wire 164.

At least the embodiment, the modifications, and the like described above can further improve the reliability of the static magnetic field magnet 10.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

Regarding the embodiment and the like described above, the following notes are disclosed as an aspect and selective characteristics of the invention.

Note 1.

A permanent current switch apparatus configured to be electrically connected to a superconducting coil via a superconducting wire, the permanent current switch apparatus including
a plurality of parallel structures with thermal permanent current switches connected in parallel, the thermal permanent current switches being capable of switching between conducting and interrupting an electric current flowing through the superconducting wire, wherein
the parallel structures are connected in series.

Note 2.

The thermal permanent current switches may each include: a heater; and a switch part configured to switch the thermal permanent current switch between a superconducting state and a normal conducting state by heat emitted by the heater. The permanent current switch apparatus may further include a heater connecting wire configured to connect the heaters provided to the respective thermal permanent current switches in parallel to an external power source configured to supply electric power to the heaters.

Note 3.

The heaters may be divided into a plurality of groups such that an electric current flowing through each of the heaters is equal and be connected in parallel to the external power source.

Note 4.

The number of the heaters included in each of the groups may be equal.

Note 5.

A magnetic resonance imaging apparatus including a superconducting magnet, wherein
the superconducting magnet includes a permanent current switch apparatus configured to be electrically connected to a superconducting coil via a superconducting wire,
the permanent current switch apparatus includes a plurality of parallel structures with thermal permanent current switches connected in parallel, the thermal permanent current switches being capable of switching between conducting and interrupting an electric current flowing through the superconducting wire, and
the parallel structures are connected in series.

Note 6.

The thermal permanent current switches of the magnetic resonance imaging apparatus may each include a heater and a switch part configured to switch the thermal permanent current switch between a superconducting state and a normal conducting state by heat emitted by the heater. The permanent current switch apparatus may further include a heater connecting wire configured to connect the heaters provided to the respective thermal permanent current switches in parallel to an external power source configured to supply electric power to the heaters.

Note 7.

The heaters of the magnetic resonance imaging apparatus may be divided into a plurality of groups such that an electric current flowing through each of the heaters is equal and be connected in parallel to the external power source.

Note 8.

The number of the heaters included in each of the groups of the magnetic resonance imaging apparatus may be equal.

What is claimed is:

1. A permanent current switch apparatus electrically connected to a superconducting coil via a superconducting wire, the permanent current switch apparatus comprising:
a first parallel structure including a first thermal permanent current switch and a second thermal permanent current switch, the first thermal permanent current switch and the second thermal permanent current switch being electrically connected to the superconducting coil in parallel, and the first thermal permanent current switch and the second thermal permanent current switch being capable of switching between a superconducting state and a normal conducting state; and
a second parallel structure including a third thermal permanent current switch and a fourth thermal permanent current switch, the third thermal permanent current switch and the fourth thermal permanent current switch being electrically connected to the superconducting coil in parallel, the third thermal permanent current switch and the fourth thermal permanent current switch being capable of switching between the superconducting state and the normal conducting state, and the first parallel structure and the second parallel structure being electrically connected to the superconducting coil in series.

2. The permanent current switch apparatus according to claim 1, wherein
each of the first thermal permanent current switch, the second thermal permanent current switch, the third thermal permanent current switch, and the fourth thermal permanent current switch comprises:
a heater; and
a switch part configured to switch between the superconducting state and the normal conducting state by heat emitted by the heater, and
wherein the heaters in the first parallel structure and the heaters in the second parallel structure are electrically connected to an external power source in parallel, the external power source being configured to supply electric power to the heaters in the first parallel structure and the heaters in the second parallel structure.

3. The permanent current switch apparatus according to claim 2, wherein the heaters are divided into a plurality of groups such that an electric current flowing through each of the heaters is equal.

4. The permanent current switch apparatus according to claim 3, wherein number of the heaters included in each of the groups is equal.

5. A magnetic resonance imaging apparatus comprising a superconducting magnet, wherein
the superconducting magnet comprises a permanent current switch apparatus electrically connected to a superconducting coil via a superconducting wire, and
the permanent current switch apparatus comprises
a first parallel structure including a first thermal permanent current switch and a second thermal permanent current switch, the first thermal permanent current switch and the second thermal permanent current switch being electrically connected to the superconducting coil in parallel, and the first thermal permanent current switch and the second thermal permanent current switch being capable of switching between a superconducting state and a normal conducting state; and
a second parallel structure including a third thermal permanent current switch and a fourth thermal permanent current switch, the third thermal permanent current switch and the fourth thermal permanent current switch being electrically connected to the superconducting coil in parallel, the third thermal permanent current switch and the fourth thermal permanent current switch being capable of switching between the superconducting state and the normal conducting state, and the first parallel structure and the second parallel structure being electrically connected to the superconducting coil in series.

6. The magnetic resonance imaging apparatus according to claim 5, wherein
each of the first thermal permanent current switch, the second thermal permanent current switch, the third thermal permanent current switch, and the fourth thermal permanent current switch comprises:
a heater; and
a switch part configured to switch between the superconducting state and the normal conducting state by heat emitted by the heater, and
wherein the heaters in the first parallel structure and the heaters in the second parallel structure are electrically connected to an external power source in parallel, the external power source being configured to supply electric power to the heaters in the first parallel structure and the heaters in the second parallel structure.

7. The magnetic resonance imaging apparatus according to claim 6, wherein the heaters are divided into a plurality of groups such that an electric current flowing through each of the heaters is equal.

8. The magnetic resonance imaging apparatus according to claim 7, wherein number of the heaters included in each of the groups is equal.

\* \* \* \* \*